United States Patent
Gil et al.

(10) Patent No.: US 8,016,831 B2
(45) Date of Patent: Sep. 13, 2011

(54) INSTRUMENTS AND TECHNIQUES FOR GUIDING INSTRUMENTS TO A SPINAL COLUMN

(75) Inventors: Carlos E. Gil, Collierville, TN (US); Rick C. Sasso, Carmel, IN (US); Mark C. Dace, Collierville, TN (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 867 days.

(21) Appl. No.: 11/703,976

(22) Filed: Feb. 8, 2007

(65) Prior Publication Data

US 2008/0234684 A1 Sep. 25, 2008

(51) Int. Cl.
*A61F 5/00* (2006.01)
*A61B 17/90* (2006.01)
*A61B 19/00* (2006.01)

(52) U.S. Cl. .................................................. 606/86 A
(58) Field of Classification Search ............... 606/79, 606/80, 86 A, 87, 99, 90, 100, 105
See application file for complete search history.

(56) References Cited

U.S. PATENT DOCUMENTS

| | | | |
|---|---|---|---|
| 5,571,109 A * | 11/1996 | Bertagnoli | 606/86 A |
| 5,817,097 A | 10/1998 | Howard et al. | |
| 6,063,088 A * | 5/2000 | Winslow | 606/86 A |
| 6,083,228 A * | 7/2000 | Michelson | 606/79 |
| 6,159,214 A | 12/2000 | Michelson | |
| 6,641,582 B1 | 11/2003 | Hanson et al. | |
| 6,736,821 B2 | 5/2004 | Squires et al. | |
| 6,746,454 B2 * | 6/2004 | Winterbottom et al. | 606/99 |
| 6,755,839 B2 | 6/2004 | Van Hoeck et al. | |
| 6,755,841 B2 * | 6/2004 | Fraser et al. | 606/99 |
| 6,966,912 B2 * | 11/2005 | Michelson | 606/80 |
| 7,070,598 B2 * | 7/2006 | Lim et al. | 606/99 |
| 7,118,580 B1 * | 10/2006 | Beyersdorff et al. | 606/99 |
| 7,153,304 B2 * | 12/2006 | Robie et al. | 606/90 |
| 7,314,468 B2 * | 1/2008 | Michelson | 606/90 |
| 7,547,309 B2 * | 6/2009 | Bertagnoli et al. | 606/99 |
| 7,635,389 B2 * | 12/2009 | Yu et al. | 623/17.15 |
| 2003/0032962 A1 * | 2/2003 | McGahan et al. | 606/80 |
| 2003/0135277 A1 | 7/2003 | Bryan et al. | |
| 2003/0187453 A1 * | 10/2003 | Schlapfer et al. | 606/90 |
| 2004/0002711 A1 | 1/2004 | Berry | |
| 2004/0002712 A1 * | 1/2004 | Grinberg et al. | 606/79 |
| 2004/0010259 A1 | 1/2004 | Keller et al. | |
| 2004/0220567 A1 * | 11/2004 | Eisermann et al. | 606/61 |
| 2005/0027300 A1 * | 2/2005 | Hawkins et al. | 606/86 |
| 2005/0096746 A1 | 5/2005 | Bryan et al. | |
| 2005/0203532 A1 | 9/2005 | Ferguson et al. | |
| 2005/0203533 A1 * | 9/2005 | Ferguson et al. | 606/90 |
| 2006/0004455 A1 * | 1/2006 | Leonard et al. | 623/17.15 |
| 2006/0235423 A1 * | 10/2006 | Cantu | 606/90 |
| 2007/0149978 A1 * | 6/2007 | Shezifi et al. | 606/90 |
| 2007/0239276 A1 * | 10/2007 | Squires et al. | 623/17.13 |

* cited by examiner

*Primary Examiner* — Thomas C Barrett
*Assistant Examiner* — Christopher Beccia

(57) ABSTRACT

Systems and methods of shaping surfaces of vertebral bodies include a reference guide instrument that can be positioned relative to a disc space between vertebral bodies and referenced to the caudally located endplate of the disc space. The reference guide instrument can then be employed to guide preparation instruments to the vertebral bodies in an orientation and spacing referenced to the caudal endplate of the subject disc space to shape vertebral surfaces to receive an implant.

15 Claims, 6 Drawing Sheets

US 8,016,831 B2

INSTRUMENTS AND TECHNIQUES FOR GUIDING INSTRUMENTS TO A SPINAL COLUMN

BACKGROUND

Normal intervertebral discs between endplates of adjacent vertebrae distribute forces between the vertebrae and cushion vertebral bodies. The spinal discs may be displaced or damaged due to trauma, disease or aging. A herniated or ruptured annulus fibrosis may result in nerve damage, pain, numbness, muscle weakness, and even paralysis. Furthermore, as a result of the normal aging processes, discs dehydrate and harden, thereby reducing the disc space height and producing instability of the spine and decreased mobility. Most surgical corrections of a disc space include a discectomy, which can be followed by restoration of normal disc space height and bony fusion of the adjacent vertebrae or disc replacement between the adjacent vertebrae to maintain the disc space height and motion. Procedures may also involve, either alone or in conjunction with intradiscal implants, positioning implants that extend extradiscally along one or more vertebrae.

Proper alignment and attachment of the implants can be difficult because of variations in the shape and contours of the vertebral body. Poor surface contact between the device and the vertebral body results if the device is mounted over variations in the surface of the vertebral body. While it is not necessary that the entire implant surface contact the vertebral body, better results can be obtained by greater contact. Therefore, it is desirable to shape the surfaces of one or more of the vertebrae to better fit the implant.

Preparation instruments can be guided along a trajectory referenced to the disc space that is determined by bi-secting the angle between the vertebral endplates when the spinal column is in a neutral flexion/extension position. The trajectory reference can also be derived from posterior vertebral body landmarks. While such techniques for establishing the trajectory for guiding preparation instruments have been helpful, there remains room for additional improvements.

SUMMARY

The present invention is directed to a system and method for guiding instruments that shape or contour surfaces of vertebral bodies. A reference guide instrument can be positioned in a disc space between vertebral bodies. In one embodiment, the reference guide instrument is positioned relative to a superior endplate of a caudally located vertebral body, also referred to herein as the caudal endplate of the disc space. The reference guide instrument can then be employed to guide preparation instruments to the vertebral bodies in an orientation referenced to the caudal endplate of the subject disc space.

In one aspect, a method for guiding instruments to a disc space between a cephalad vertebra and a caudal vertebra comprises: aligning a reference guide instrument with a caudal endplate of the disc space by positioning a reference mechanism of the reference guide instrument in the disc space, the reference guide instrument including a guiding portion extending proximally from the reference mechanism and the disc space along a reference axis; securing a caudal member of the reference mechanism along the caudal endplate of the disc space with the reference axis extending parallel to the caudal endplate of the disc space; and guiding a preparation instrument along the guiding portion and reference axis to a location adjacent the cephalad and caudal vertebrae.

In another aspect, a method for guiding instruments to a disc space between a cephalad vertebra and a caudal vertebra comprises: biasing a caudal member of a reference guide instrument into engagement with an endplate of the caudal vertebra with a guiding portion of the reference guide instrument extending along a reference axis in parallel relation to the endplate of the caudal vertebra, wherein the caudal member includes a height between an endplate contacting surface and an opposite surface that is substantially less than a height of the disc space between endplates of the cephalad and caudal vertebrae; and guiding a preparation instrument along the guiding portion and reference axis to a location adjacent the cephalad and caudal vertebrae.

According to another aspect, a method for guiding instruments to a disc space between a cephalad vertebra and a caudal vertebra comprises: positioning a reference mechanism of a reference guide instrument in the disc space with a guiding portion of the reference guide instrument extending proximally from the disc space; engaging a caudal member of the reference mechanism against an endplate of the caudal vertebra with a reference axis of the guiding portion extending parallel to the endplate of the caudal vertebra and with the caudal member including a height therealong that is less than a height of the disc space between endplates of the cephalad and caudal vertebrae so that the caudal member is spaced from the endplate of the cephalad vertebra when engaged to the endplate of the caudal vertebra; and guiding a preparation instrument along the guiding portion and reference axis to a location adjacent the cephalad and caudal vertebrae.

These and other aspects are further discussed below.

DETAILED DESCRIPTION OF THE ILLUSTRATED EMBODIMENTS

Figure 1:
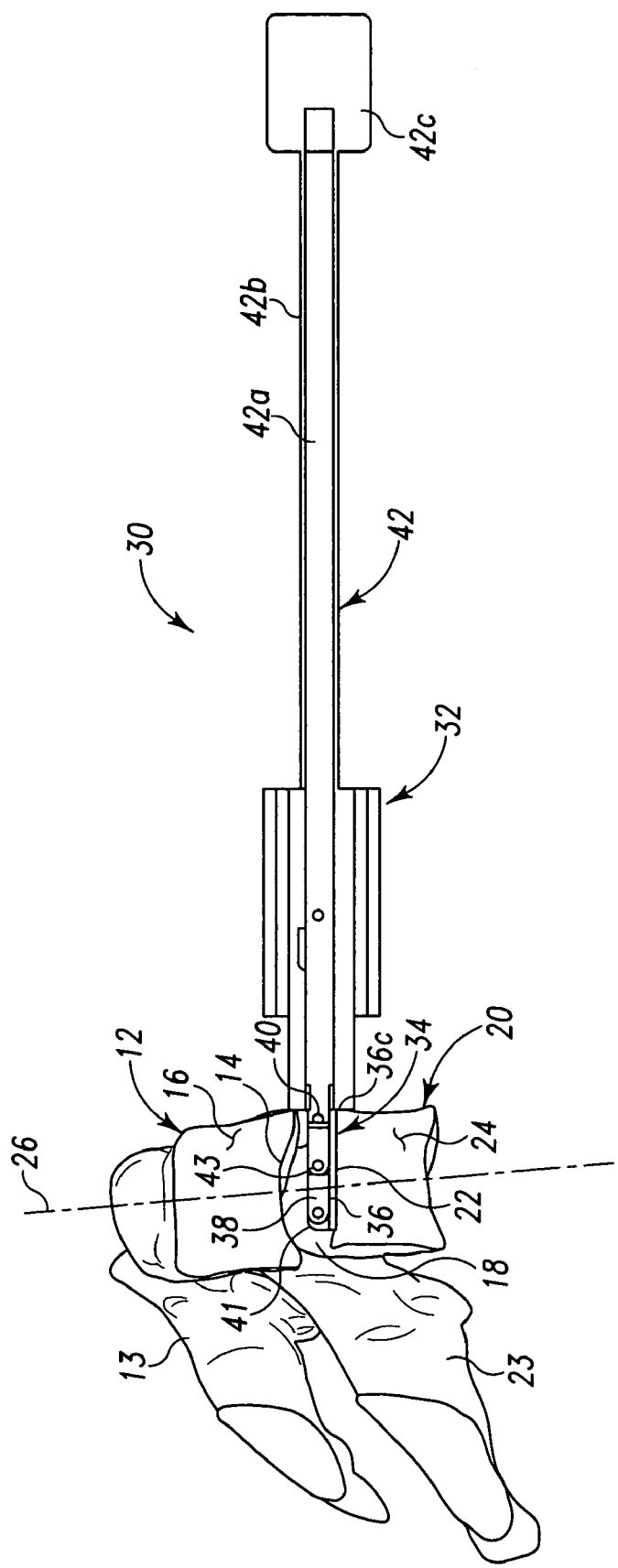
FIG. 1 is a diagrammatic elevation view of a reference guide instrument positioned in spinal disc space between vertebrae of a spinal column.

For the purposes of promoting an understanding of the principles of the present invention, reference will now be made to the embodiments illustrated in the drawings, and specific language will be used to describe the same. It will nevertheless be understood that no limitation of the scope of the invention is intended thereby. Any alterations and further modification in the described processes, systems, or devices, and any further applications of the principles of the invention as described herein are contemplated as would normally occur to one skilled in the art to which the invention relates.

The present invention is directed to a system and method of shaping and contouring a perimeter surface of a vertebral body for receipt of an implant. The shaped surface can include any one or combination of the endplate of a cephalad vertebra, the surfaces of the cephalad vertebra outside the disc space, the endplate of a caudal vertebra, and surfaces of the caudal vertebra outside the disc space. A reference guide instrument is positioned in the space between vertebrae and aligned with the endplate of the caudal vertebra so that the reference guide instrument forms a parallel relationship with the caudal endplate. The parallel reference to the caudal endplate can then be translated to the cephalad endplate, or to some other location along either of the cephalad and caudal vertebrae, to shape surfaces to receive the implant in the referenced relationship.

In one application, preparation instruments are guided to a location adjacent the vertebrae with the reference guide instrument. The preparation instruments can be positioned relative to the reference guide instrument to contact one or more of the vertebral bodies. The preparation instruments can guide cutting tools or be in the form of a cutting tool operable to contour or shape one or more surfaces of the vertebrae while the relationship with the caudal endplate is maintained. With alignment maintained in this manner, the bone surfaces can be prepared at a predetermined position relative to the endplate of the caudal vertebra.

Referring now to FIG. 1, there is shown an elevation view of a spinal column segment 10 with a cephalad vertebra 12 and a caudal vertebra 20. Disc space 18 is situated between vertebrae 12 and 20. Cephalad vertebra 12 includes an endplate 14 and an exterior surface 16 outside the disc space 18. Caudal vertebra 20 includes an endplate 22, also referred to as the caudal endplate of the disc space, and an exterior surface 24 outside the disc space 18. Vertebrae 12, 20 extend along central axis 26 of the spinal column segment 10. Vertebrae 12, 20 include posterior elements 13, 23 extending from the anterior portions of the respective vertebrae 12, 20.

There is further shown in FIG. 1 a reference guide instrument 30 that is positioned in disc space 18. Reference guide instrument 30 includes a guiding portion 32 extending away or proximally from the disc space 18, and a distal referencing mechanism 34 positioned at least in part in disc space 18. Referencing mechanism 34 includes a caudal endplate member 36 located distally of guiding portion 32, and a securing member 38 pivotally coupled between guiding portion 32 and caudal member 36 at joints 40 and 41. An actuator portion 42 extends proximally from joint 40 and is linked with securing member 38 so that operation of actuator portion 42 linearly translates and pivotally displaces securing member 38 about an intermediate joint 43 from an orientation extending along caudal member 36, as shown in FIG. 1, to a location pivoted away from caudal member 36, as shown in FIG. 2.

Figure 2:
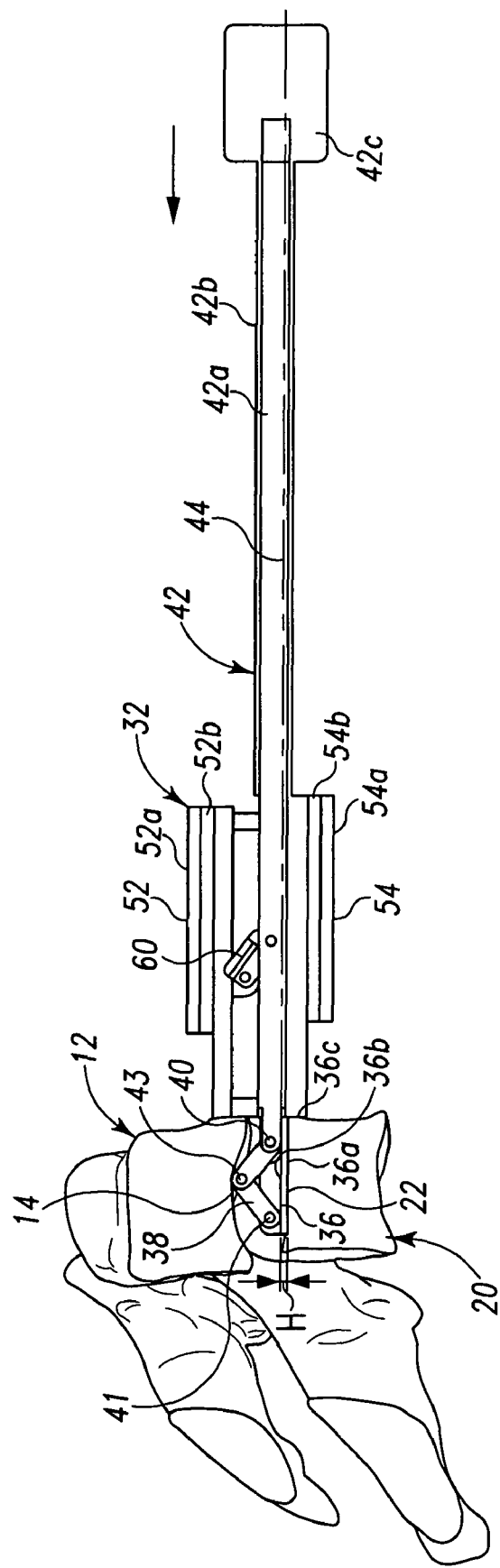
FIG. 2 is a diagrammatic elevation view of the reference guide instrument and vertebrae of FIG. 1 with the reference guide engaged to the adjacent vertebrae.

In the secured position shown in FIG. 2, securing member 38 contacts the endplate 14 of cephalad vertebra 12 to secure and bias caudal member 36 in contact with caudal endplate 22. In this secured relationship, caudal member 36 is forced and maintained in firm engagement with the caudal endplate 22 so that caudal member 36 and guiding portion 32 extend parallel with caudal endplate 22 along a reference axis 44. Securing member 38 is pivoted by linearly translating joint 40 toward joint 41, causing securing member 38 to pivot about intermediate joint 43 and displace it toward endplate 14.

In the illustrated embodiment, actuator portion 42 includes a fixed member 42b from which caudal member 36 distally extends in a fixed relationship and a translatable member 42a having a distal end pivotally coupled at proximal joint 40. Distal joint 41 is pivotally coupled to the distal end of caudal member 36. Handle 42c is rotatably mounted to fixed member 42b, and is threadingly engaged to translatable member 42a. Rotation of handle 42c about fixed member 42b causes translatable member 42a to axially displace relative to fixed member 42b and caudal member 36. The axial displacement of translatable member 42a causes securing member 38 to change in length by pivoting about proximal and distal joints 40, 41 and pivoting and displacing intermediate joint 43 toward the cephalad endplate 14.

Caudal member 36 includes a height H extending thereal ong between a caudal surface 36a and an opposite cephalad surface 36b. Surfaces 36a, 36b extend parallel to one another. Height H is sized so that it is substantially less than the height of disc space 18 between endplates 14, 22. Height H is sized so that cephalad surface 36b is spaced from endplate 14 of cephalad vertebra 12 along caudal member 36, ensuring the caudal member 36 can be positioned along the caudal endplate 22 without endplate 14 influencing the positioning thereof. Caudal member 36 also includes a caudally oriented lip 36c to contact the exterior surface 24 of caudal vertebra 20 and limit insertion into the disc space or to provide an indication of proper insertion depth.

In the illustrated embodiment of FIG. 1, referencing mechanism 34 has a scissors-like configuration with a fixed caudal member 36 that forms an extension of actuating portion 42 along with a pivotally movable securing member 38. Other engagement and movement relationships between the securing member 38 and the caudal member 36 are also contemplated. For example, securing member 38 can be moved orthogonally to caudal member 36 by a turnbuckle, rack and pinion mechanism or the like in order to firmly seat caudal member 36 to the caudal endplate 22. In another embodiment, securing member 38 has a distally tapered wedge shape that is axially and distally movable along caudal member 36 to wedge caudal member 36 against caudal endplate 22.

Once referencing mechanism 34 is secured in disc space 18 with caudal member 36 engaged along caudal endplate 22, guiding portion 32 of reference guide instrument 30 extends proximally from vertebrae 12, 20 as shown in FIG. 2. Guiding portion 32 is shown with an upper guiding member 52 and a lower guiding member 54. Guiding members 52, 54 include outer flange members 52a, 54a and an extension member 52b, 54b, respectively. Flange members 52a, 54a from a slot or groove with the respective extension member 52b, 54b to guide a preparation instrument therealong to the respective vertebra 12, 20.

In the illustrated embodiment, cephalad guiding member 52 is pivotally mounted to translatable member 42a with a linkage 60. As translatable member 42a is axially and distally displaced to engage securing member 38 to the cephalad vertebra 12, guiding member 52 is displaced cephaladly by linkage 60 to a desired alignment with cephalad vertebra 12. In another embodiment, linkage 60 is secured to the fixed member 42b, and allows guide body 82 to be pivoted and aligned in the desired position with cephalad vertebra 12 after guide body 84 is secured to caudal vertebra 20. In either embodiment, linkage 60 can be removably coupled to guide body 82 to allow removal of reference guide instrument 30 from between guide bodies 82, 84.

Figure 3:
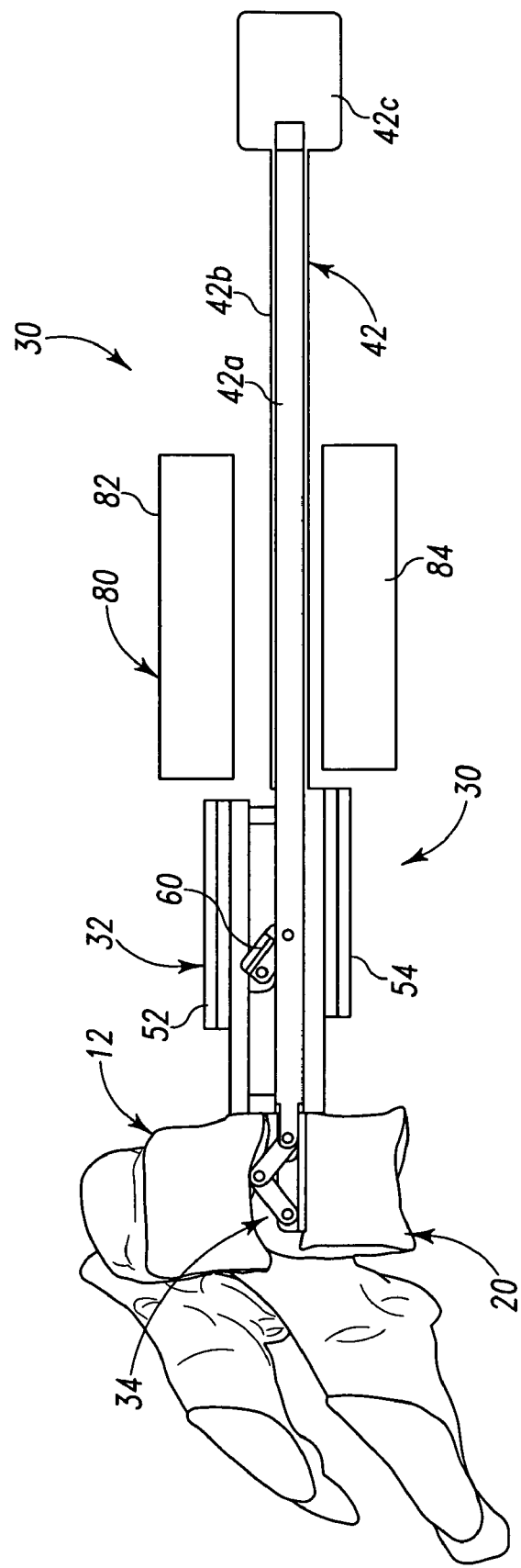
FIG. 3 is a diagrammatic elevation view of the reference guide instrument of FIG. 2 with a preparation instrument before positioning along the reference guide instrument.
Figure 4:
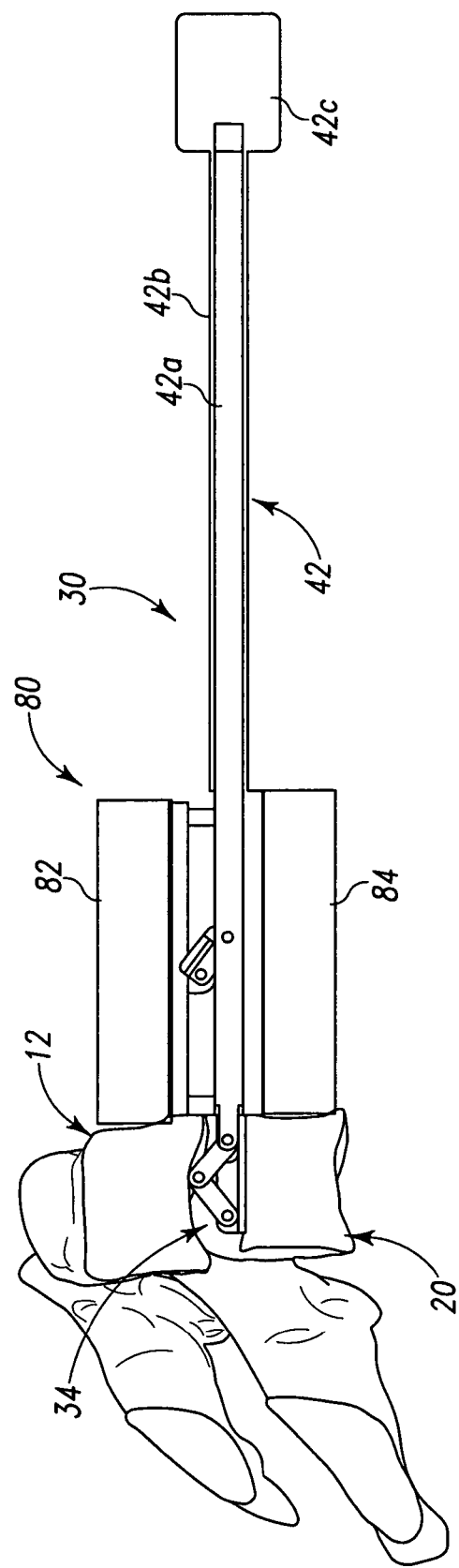
FIG. 4 is a diagrammatic elevation view of the reference guide instrument of FIG. 2 with the preparation instrument positioned along the reference guide instrument.
Figure 5:
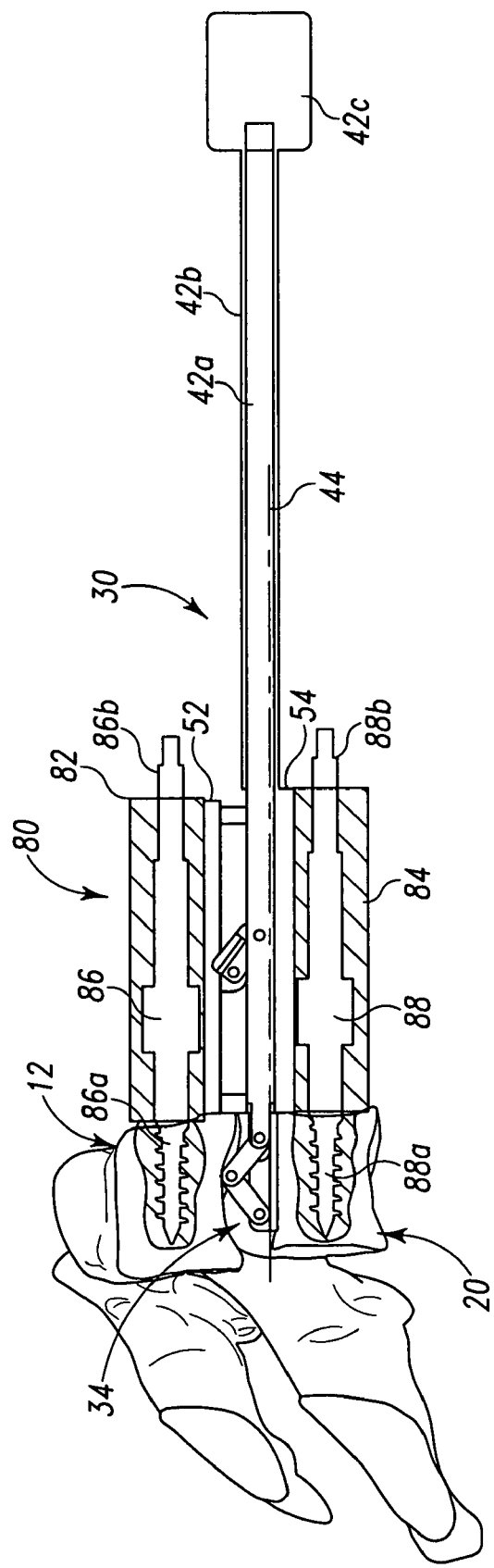
FIG. 5 is a diagrammatic longitudinal section view of the reference guide instrument and preparation instrument with the preparation instrument engaged to the vertebrae.

In the secured relationship with caudal endplate 22, guiding portion 32 extends along reference axis 44 and can be employed to guide one or more preparation or mounting instruments to a location adjacent to vertebrae 12, 20, such as shown in FIGS. 3 and 4. In FIGS. 3 and 4 there is shown a preparation instrument in the form of a milling guide 80 having a cephalad guide body 82 and a caudal guide body 84 positioned about respective ones of the guiding members 52, 54 of guiding portion 32. When the distal ends of guide bodies 82, 84 of guide 80 are positioned in contact with or adjacent the respective vertebral body 12, 20, fasteners 86, 88 are positioned through respective ones of the passages 82a, 84a and engaged to the respective vertebra 12, 20 to engage guide bodies 82, 84 thereto, as shown in FIG. 5. Fasteners 86, 88 include a distal threaded portion 86a, 88a and a proximal stem 86b, 88b, respectively, extending proximally through the respective guide body 82, 84 to allow access to the fasteners so they can be manipulated for engagement and disengagement with the respective vertebra. In one embodiment, fasteners 86, 88 are removable from the guide bodies 82, 84. In another embodiment, fasteners 86, 88 form part of the assembly of the respective guide body 82, 84 of milling guide 80.

Figure 6:
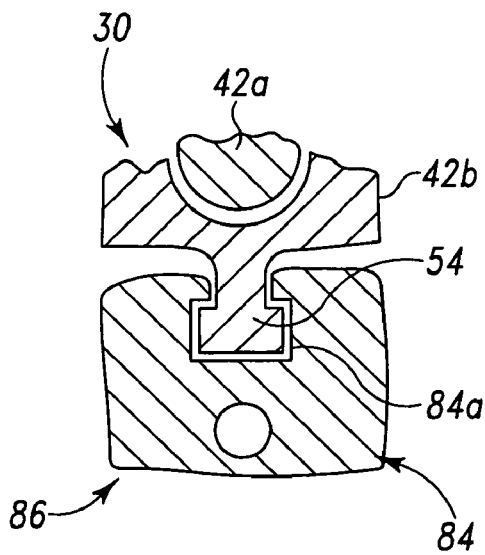
FIG. 6 is a cross-sectional view of a portion of the reference guide instrument showing a portion of the preparation instrument engaged thereto.

As shown in FIG. 6, guide bodies 82, 84 each include a channel, such as shown with channel 84a of guide body 84, that is received around the respective guiding member 54 of guiding portion 32. Guide bodies 82, 84 are slidably positioned along the respective guiding member 52, 54 of guiding portion 32 so that milling guide 80 can be guided along reference axis 44 in parallel relation thereto and to the endplate 22 of caudal vertebra 20. Fasteners 86, 88 secure the guide bodies 82, 84 to respective ones of the vertebrae 12, 20 to maintain the positioning of milling guide 80 in a referenced parallel relationship to caudal endplate 22 of disc space 18. Other guiding relationships are also contemplated between guiding portion 32 and the preparation instrument. For example, guiding portion 32 can include a seat that locates the preparation instrument thereon in position relative to the respective vertebra as the preparation instrument is moved into position for seating on the guiding portion.

Milling guide 80 guides contouring or shaping mechanisms that are positioned and guided along channels, such as channel 84a after removal of reference guide instrument 20, or other structure of the respective guide bodies 82, 84. The contouring and shaping mechanisms are operably guided by the respective guide bodies 82, 84 to remove bony material and shape and contour surfaces of the respective vertebrae 12, 20 to accommodate an implant. Various embodiments of contouring mechanisms may be useful in the present invention including, but not limited to, burrs, router bits, abraders, grinders, rasps, drills, graters, saws, oscillating cutters, vibrating cutters, reciprocating cutters, orbital cutters, rotating cutters, and lasers. Milling guide 80 can also include a handle or other structure extending proximally from one or both of the guide bodies 82, 84 to facilitate moving and holding milling guide 80 into position along reference guide instrument 30. Other examples of milling guide configurations are provided in U.S. Pat. No. 6,159,214, which is incorporated herein by reference. Still other guiding and bone preparation instruments are contemplated for use in preparing bone, examples of which are provided in U.S. Pat. Nos. 6,755, 839 and 6,736,821 which are incorporated herein by reference.

In use, the reference guide instrument 30 is positioned relative to one or more vertebral bodies 12, 20. The reference guide instrument 30 is aligned with caudal endplate member 36 positioned along caudal endplate 22. Actuator portion 42 is actuated to pivot and translate securing member 38 toward cephalad endplate 14 to contact endplate 14 and firmly seat caudal endplate member 36 against caudal endplate 22. In this arrangement, guiding portion 32 extends proximally from disc space 18 and along reference axis 44 oriented parallel to the caudal endplate 22. Preparation instruments can then be secured to guiding portion 32 and guided along reference axis 44 to a location adjacent to vertebrae 12, 20 while maintaining the reference of the preparation instrument with the caudal endplate 22 of caudal vertebra 20. The alignment of the preparation instrument is caused by the predetermined relationship between the reference guide instrument 30 relative to the vertebrae 12, 20 established with engagement of caudal endplate member 36 with caudal endplate 22.

In procedures employing guide bodies 82, 84, the caudal guide body 84 is secured to the caudal vertebra first so that the fastener 88 and guide body 84 are placed a controlled distance from endplate 22 of caudal vertebra 20. Once aligned by the predetermined relationship, the cephalad guide body 82 is secured to cephalad vertebra 12 such that fastener 86 is spaces a predetermined distance from endplate 22 of caudal vertebra 20. Once the guide bodies are secured to vertebrae 12, 20, reference guide instrument 30 is removed. The spacing between vertebrae 12, 20 is then adjusted to a desired distance with a distractor/compressor instrument (not shown), and discectomy and decompression procedures are completed. Guide bodies 82, 84 also guide bone preparation instruments to vertebrae 12, 20 and disc space 18 while the relationship is maintained to contour or shape surfaces of one or both of the vertebrae 12, 20.

Figure 7:
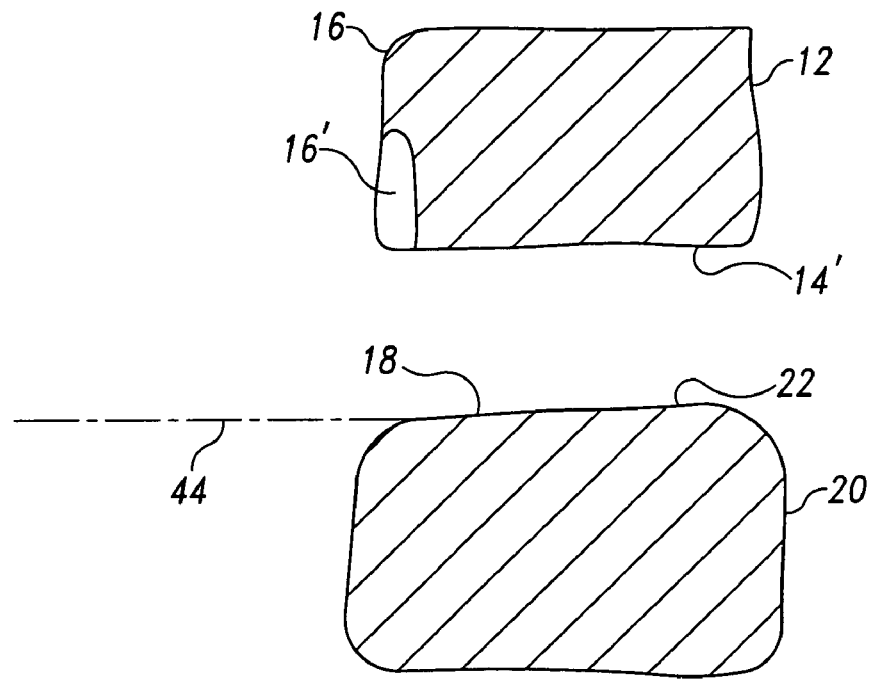
FIG. 7 is a sectional view of the vertebrae showing the reference axis extending parallel to the caudal endplate and shaped surfaces of the cephalad vertebra.

In one procedure, the preparation instruments are guided in parallel relation to reference axis 44 and thus parallel to caudal endplate 22. This allows formation of a modified endplate surface 14', as shown in FIG. 7, on cephalad vertebra 12 that is parallel to reference axis 44 and thus parallel to caudal endplate 22. After removal of the preparation instruments, an implant can be positioned in disc space 18 and in secure engagement with the parallel endplate surfaces along vertebrae 12, 20. Other techniques contemplate surfaces 16' are formed on the exterior 16 of vertebrae 12, 20 to receive a plate positioned along the vertebrae, or to receive a flange from an endplate of an artificial disc device positioned in disc space 18, for example.

In one particular application, reference mechanism 34 is sized and arranged structurally to contact the endplates of the adjacent vertebral bodies in a cervical region of the spinal column. Reference mechanism 34 and members 36, 38 may have a variety of widths and heights to fit between different vertebral bodies along different regions of the spine. Guiding portion 32 is connected to and extends outwardly from reference mechanism 34. Guiding portion 32 is substantially linear and is co-axial with caudal endplate member 36. In one embodiment, guiding portion 32 has a width that is the same as caudal member 36. Other embodiments contemplate other widths and shapes for guiding portion 32, including circular, square and non-circular cross-sections. Guiding portion 32 also includes a length extending proximally from the reference mechanism 34. In one embodiment, guiding portion 32 has a length so that its proximal end opposite reference mechanism 34 extends outside of a patient's body when reference mechanism 34 is positioned between the vertebral bodies.

In one embodiment, the reference guide instrument 30 is used in procedures for contouring and shaping one or more vertebral bodies within the cervical region of the spine. In a further embodiment, the reference guide instrument 30 is used for shaping and contouring one or more vertebral bodies within the thoracic and lumbar regions of the spine. In another embodiment, reference guide instrument 30 is used for shaping and contouring the anterior section of one or more vertebral bodies. In yet another embodiment, reference guide instrument 30 is employed in procedures for contouring or shaping a lateral section or an antero-lateral section of one or more vertebral bodies.

Reference guide instrument 30 is provided with a removable guiding portion 32 in one embodiment. A set of several guiding portions is provided of various heights so that the guiding portion of the desired height is selected by the surgeon. Alternatively, several reference guide instruments are provided having guiding portions of various heights so that the instrument providing the desired location of the guiding portion relative to vertebrae 12, 20 is selected by the surgeon.

While the invention has been illustrated and described in detail in the drawings and the foregoing description, the same is considered to be illustrative and not restrictive in character. All changes and modifications that come within the spirit of the invention are desired to be protected.

What is claimed is:

1. A method for guiding instruments to a disc space between a cephalad vertebra and a caudal vertebra, comprising:
aligning a reference guide instrument with a caudal endplate of the disc space by positioning a reference mechanism of the reference guide instrument in the disc space, the reference guide instrument including a guiding portion extending proximally from the reference mechanism and the disc space along a reference axis;
securing a caudal member of the reference mechanism along the caudal endplate of the disc space with the reference axis extending parallel to the caudal endplate of the disc space, wherein the reference mechanism includes a securing member and an actuating member, wherein the actuating member includes a fixed portion and the caudal member extends from the fixed portion in a fixed relationship therewith to a distal end of the caudal member and the actuating member also includes a movable portion, the securing member including a distal end pivotally coupled to the distal end of the fixed caudal member and a proximal end pivotally coupled to the movable portion of the actuating member, the securing member further including an intermediate joint between the distal end and the proximal end of the securing member, wherein the actuating portion is linearly and distally translatable to pivot the securing member between the actuating portion and the caudal member and about the intermediate joint of the securing member to displace the intermediate joint of the securing member toward a cephalad endplate of the disc space; and
guiding a preparation instrument along the guiding portion in a predetermined relationship to the reference axis to a location adjacent the cephalad and caudal vertebrae.

2. The method of claim 1, wherein securing the caudal member includes pivoting the securing member of the reference mechanism relative to the caudal member to contact the endplate of the cephalad vertebra with the intermediate joint and force the caudal member in engagement with the caudal endplate of the disc space.

3. The method of claim 2, wherein securing the caudal member includes moving the actuator along the guiding portion to pivot the securing member.

4. The method of claim 1, wherein guiding the preparation instrument includes sliding an instrument guide body along the guiding portion and securing the instrument guide body to at least one of the cephalad and caudal vertebrae with a fastener while maintaining the predetermined relationship.

5. The method of claim 1, wherein securing the caudal member includes biasing the caudal member into contact with the caudal endplate of the disc space by contacting the endplate of the cephalad vertebra.

6. The method of claim 1, wherein aligning the reference guide instrument includes positioning the reference guide instrument in the disc space from an anterior approach and the cephalad and caudal vertebrae are cervical vertebrae.

7. The method of claim 1, wherein the guiding portion includes opposite guiding members extending along and parallel to the reference axis, one of the guiding members being caudally located along the reference guide instrument and the other of the guiding members being cephaladly located along the reference guide instrument.

8. The method of claim 1, wherein the caudal member includes a height in the disc space that is substantially less than a distance between endplates of the cephalad and caudal vertebrae in the disc space.

9. The method of claim 8, wherein the caudal member includes a contacting surface extending along the caudal endplate of the disc space when the caudal member is secured along the caudal endplate and an opposite surface extending parallel to the contacting surface.

10. A method for guiding instruments to a disc space between a cephalad vertebra and a caudal vertebra, comprising:
biasing a caudal member of a reference guide instrument into engagement with an endplate of the caudal vertebra with a guiding portion of the reference guide instrument extending along a reference axis in parallel relation to the endplate of the caudal vertebra, wherein the caudal member includes a height between an endplate contacting surface and an opposite surface that is substantially less than a height of the disc space between endplates of the cephalad and caudal vertebrae, wherein the reference guide instrument includes a securing member and an actuating member, wherein the actuating member includes a fixed portion and the caudal member extends from the fixed portion in a fixed relationship therewith to a distal end of the caudal member and the actuating member also includes a movable portion, the securing member including a distal end pivotally coupled to the distal end of the fixed caudal member and a proximal end pivotally coupled to the movable portion of the actuating member, the securing member further including an intermediate joint between the distal end and the proximal end of the securing member, wherein the actuating portion is linearly and distally translatable to pivot the securing member between the actuating portion and the caudal member and about the intermediate joint of the securing member to displace the intermediate joint of the securing member to contact the cephalad endplate and bias the caudal member into engagement with the caudal endplate; and
guiding a preparation instrument along the guiding portion and reference axis to a location adjacent the cephalad and caudal vertebrae.

11. The method of claim 10, wherein guiding the preparation instrument includes sliding a milling guide along the guiding portion and securing the milling guide to at least one of the cephalad and caudal vertebrae with a fastener.

12. The method of claim 10, wherein the guiding portion includes opposite guiding members extending parallel to the reference axis, one of the guiding members being caudally oriented along the reference guide instrument and the other of the guiding members being cephaladly oriented along the reference guide instrument.

13. A method for guiding instruments to a disc space between a cephalad vertebra and a caudal vertebra, comprising:
- positioning a reference mechanism of a reference guide instrument in the disc space with a guiding portion of the reference guide instrument extending proximally from the disc space;
- engaging a caudal member of the reference mechanism against an endplate of the caudal vertebra with a reference axis of the guiding portion extending parallel to the endplate of the caudal vertebra and with the caudal member including a height therealong that is less than a height of the disc space between endplates of the cephalad and caudal vertebrae so that the caudal member is spaced from the endplate of the cephalad vertebra when engaged to the endplate of the caudal vertebra, wherein the reference mechanism includes a securing member and an actuating member, wherein the actuating member includes a fixed portion and the caudal member extends from the fixed portion in a fixed relationship therewith to a distal end of the caudal member and the actuating member also includes a movable portion, the securing member including a distal end pivotally coupled to the distal end of the fixed caudal member and a proximal end pivotally coupled to the movable portion of the actuating member, the securing member further including an intermediate joint between the distal end and the proximal end of the securing member, wherein the actuating portion is linearly and distally translatable to pivot the securing member between the actuating portion and the caudal member and about the intermediate joint of the securing member to displace the intermediate joint of the securing member toward the endplate of the cephalad vertebra; and
- guiding a preparation instrument along the guiding portion and reference axis to a location adjacent the cephalad and caudal vertebrae.

14. The method of claim 13, wherein the guiding portion includes at least one guiding member extending parallel to the reference axis.

15. The method of claim 14, wherein the preparation instrument includes a guide body defining a channel slidably receiving the guiding member as the preparation instrument is guided along the guiding portion of the reference guide instrument.

* * * * *